United States Patent
Heindl et al.

(10) Patent No.: US 11,127,137 B2
(45) Date of Patent: Sep. 21, 2021

(54) MALIGNANCY ASSESSMENT FOR TUMORS

(71) Applicant: KHEIRON MEDICAL TECHNOLOGIES LTD, London (GB)

(72) Inventors: Andreas Heindl, London (GB); Galvin Khara, London (GB); Joseph Yearsley, London (GB); Michael O'Neill, London (GB); Peter Kecskemethy, London (GB); Tobias Rijken, London (GB)

(73) Assignee: KHEIRON MEDICAL TECHNOLOGIES LTD, London (GB)

( * ) Notice: Subject to any disclaimer, the term of this patent is extended or adjusted under 35 U.S.C. 154(b) by 27 days.

(21) Appl. No.: 16/604,664

(22) PCT Filed: Apr. 12, 2018

(86) PCT No.: PCT/GB2018/050981
§ 371 (c)(1),
(2) Date: Oct. 11, 2019

(87) PCT Pub. No.: WO2018/189551
PCT Pub. Date: Oct. 18, 2018

(65) Prior Publication Data
US 2020/0342589 A1    Oct. 29, 2020

(30) Foreign Application Priority Data

Apr. 12, 2017  (GB) ..................... 1705911
Jul. 18, 2017  (GB) ..................... 1711559

(51) Int. Cl.
*G06T 7/00*   (2017.01)
*G06T 7/11*   (2017.01)
(Continued)

(52) U.S. Cl.
CPC ............ *G06T 7/0014* (2013.01); *A61B 5/055* (2013.01); *A61B 5/4312* (2013.01);
(Continued)

(58) Field of Classification Search
CPC ....... G06T 7/0014; G06T 7/136; G06T 7/143; G06T 7/11; G06T 7/337; G06T 7/0012;
(Continued)

(56) References Cited

U.S. PATENT DOCUMENTS 6,075,879 A     6/2000  Roehrig et al.
6,463,425 B2 *  10/2002 Raz ................. G01N 15/1475
                                                 382/128
(Continued)

FOREIGN PATENT DOCUMENTS

CN    105931226 A    9/2016
CN    106096491 A   11/2016
(Continued)

OTHER PUBLICATIONS

Ronneberger Olaf et al: "U-Net: Convolutional Networks for Biomedical Image Segmentation", Nov. 18, 2015 (Nov. 18, 2015), Medical Image Computing and Computer-Assisted Intervention—MICCAI 2015 :18th International Conference, Munich, Germany, Oct. 5-9, 2015; (Year: 2015).*
(Continued)

*Primary Examiner* — Vu Le
*Assistant Examiner* — Courtney Joan Nelson
(74) *Attorney, Agent, or Firm* — Finch & Maloney PLLC

(57) ABSTRACT

The present invention relates to deep learning for automated assessment of malignancy of lesions.
According to a first aspect, there is provided a computer-aided method of malignancy assessment of lesions, the method comprising the steps of: receiving input data; performing a first analysis on the input data to identify one or
(Continued)

more lesions, generating a probability map for the one or more lesions from the input data; performing a second analysis on the input data to obtain a malignancy probability mask for the input data; and generating an overlay for the input data by combining the lesion probability map with the malignancy probability mask.

20 Claims, 3 Drawing Sheets

(51) Int. Cl.
*G16H 30/20* (2018.01)
*G16H 50/20* (2018.01)
*G16H 30/40* (2018.01)
*A61B 5/00* (2006.01)
*A61B 6/00* (2006.01)
*G06N 3/08* (2006.01)
*G06T 7/143* (2017.01)
*A61B 5/055* (2006.01)
*A61B 6/03* (2006.01)
*G06T 7/136* (2017.01)
*G06T 7/33* (2017.01)
*G16H 50/30* (2018.01)

(52) U.S. Cl.
CPC .......... *A61B 5/7264* (2013.01); *A61B 5/7267* (2013.01); *A61B 5/7282* (2013.01); *A61B 6/032* (2013.01); *A61B 6/502* (2013.01); *A61B 6/5217* (2013.01); *G06N 3/08* (2013.01); *G06T 7/0012* (2013.01); *G06T 7/0016* (2013.01); *G06T 7/11* (2017.01); *G06T 7/136* (2017.01); *G06T 7/143* (2017.01); *G06T 7/337* (2017.01); *G16H 30/20* (2018.01); *G16H 30/40* (2018.01); *G16H 50/20* (2018.01); *G16H 50/30* (2018.01); *G06T 2207/10081* (2013.01); *G06T 2207/10088* (2013.01); *G06T 2207/10116* (2013.01); *G06T 2207/20081* (2013.01); *G06T 2207/20084* (2013.01); *G06T 2207/30068* (2013.01); *G06T 2207/30096* (2013.01)

(58) Field of Classification Search
CPC ......... G06T 7/0016; G06T 2207/10081; G06T 2207/10088; G06T 2207/10116; G06T 2207/20081; G06T 2207/20084; G06T 2207/30068; G06T 2207/30096; G16H 30/20; G16H 50/30; G16H 50/20; G16H 30/40; A61B 5/055; A61B 5/4312; A61B 5/7264; A61B 5/7267; A61B 5/7282; A61B 6/032; A61B 6/502; A61B 6/5217; G06N 3/08
See application file for complete search history.

(56) References Cited

U.S. PATENT DOCUMENTS

| | | | |
|---|---|---|---|
| 9,589,374 B1 | 3/2017 | Gao et al. | |
| 2005/0113651 A1 | 5/2005 | Wood et al. | |
| 2007/0003119 A1 | 1/2007 | Roehrig et al. | |
| 2011/0123087 A1 | 5/2011 | Nie et al. | |
| 2011/0150313 A1 | 6/2011 | Su et al. | |
| 2013/0343626 A1 | 12/2013 | Rico et al. | |
| 2014/0355840 A1 | 12/2014 | Peyton | |
| 2016/0350946 A1 | 12/2016 | Schieke et al. | |
| 2018/0129900 A1 | 5/2018 | Kiraly et al. | |
| 2018/0165809 A1 | 6/2018 | Stanitsas et al. | |
| 2018/0218497 A1 | 8/2018 | Golden et al. | |
| 2020/0074632 A1 | 3/2020 | Heindl et al. | |
| 2020/0074634 A1 | 3/2020 | Kecskemethy et al. | |
| 2020/0167928 A1 | 5/2020 | Heindl et al. | |

FOREIGN PATENT DOCUMENTS

| | | | | |
|---|---|---|---|---|
| CN | 106204587 A | 12/2016 | | |
| WO | 2008050332 A2 | 5/2008 | | |
| WO | WO-2008050332 A2 * | 5/2008 | .......... | G06T 7/0012 |
| WO | 2008088478 A1 | 7/2008 | | |
| WO | 2015031641 A1 | 3/2015 | | |
| WO | 2015077076 A1 | 5/2015 | | |
| WO | WO-2017210690 A1 * | 12/2017 | ............ | G06T 7/143 |
| WO | 2018189541 A1 | 10/2018 | | |
| WO | 2018189549 A1 | 10/2018 | | |
| WO | 2018189550 A1 | 10/2018 | | |
| WO | 2018189551 A1 | 10/2018 | | |

OTHER PUBLICATIONS

Patrick Ferdinand Christ et al: "Automatic Liver and Tumor Segmentation of CT and MRI Volumes using Cascaded Fully Convolutional Neural Networks", arxiv.org, Cornell University Library, 201 Olin Library Cornell University Ithaca, NY 14853, Feb. 20, 2017 (Year: 2017).*
Patrick Ferdinand Christ et al: "SurvivalNet: Predicting patient survival from diffusion weighted magnetic resonance images using cascaded fully convolutional and 3D convolutional neural networks", arxiv.org, Cornell University Library , 201 Olin Library Cornell University Ithaca, NY 14853, Feb. 20, 17 (Year: 2017).*
R. El hamdi, M. Njah and M. Chtourou, "Breast cancer diagnosis using a hybrid evolutionary neural network classifier," 18th Mediterranean Conference on Control and Automation, MED'10, Marrakech, 2010, pp. 1308-1315, doi: 10.1109/MED.2010.5547867. (Year: 2010).*
International Search Report and Written Opinion received for Patent Application No. PCT/GB2018/050969, dated Jun. 26, 2018. 20 pages.
International Preliminary Report on Patentability received for Patent Application No. PCT/GB2018/050969. Dated Oct. 15, 2019. 12 pages.
International Search Report and Written Opinion received for PCT Application No. PCT/GB2018/050980. Dated Jul. 12, 2018. 34 pages.
International Preliminary Report on Patentability received for PCT Application No. PCT1GB2018/050980. Dated Oct. 15, 2019. 11 pages.
Combined Search and Examination Report under Sections 17 and 18(3) received for GB Application No. 1711558.5, dated Dec. 22, 2017. 6 pages.
International Search Report and Written Opinion received for Patent Application No. PCT/GB2018/050979. Dated Jul. 9, 2018. 36 pages.
International Preliminary Report on Patentability received for Patent Application No. PCT/GB2018/050979. Dated Oct. 15, 2019. 11 pages.
Combined Search and Examination Report under Sections 17 and 18(3) received for GB Application No. 1711557.7, dated Jan. 18, 2018. 5 pages.
International Search Report and Written Opinion received for Patent Application No. PCT/GB2018/050981, dated Jul. 9, 2018. 23 pages.
International Preliminary Report on Patentability received for Patent Application No. PCT/GB2018/050981. Dated Oct. 15, 2019. 15 pages.
Combined Search and Examination Report under Sections 17 and 18(3) received for GB Application No. 1711559.3 dated Dec. 19, 2017. 7 pages.
Christ, et al., "Automatic Liver and Tumor Segmentation of CT and MRI Volumes Using Cascaded Fully Convolutional Neural Networks," arXiv: 1702.05970v2 [cs.CV], Feb. 23, 2017. 20 pages.
Christ, et al., "Survivalnet: Predicting Patient Survival From Diffusion Weighted Magnetic Resonance Images Using Cascaded

(56) References Cited

OTHER PUBLICATIONS

Fully Convolutional and 3D Convolutional Neural Networks," arXiv: 1702.05941v1 [cs.CV], Feb. 20, 2017. 6 pages.

Hou, et al., "Patch-based Convolutional Neural Network for Whole Slide Tissue Image Classification," IEEE Conference on Computer Vision and Pattern Recognition, (CVPR) Jun. 27, 2016. pp. 2424-2433.

Menechelli, et al., "Automatic breast tissue density estimation scheme in digital mammography images," Progress in Biomedical Optics and Imaging, SPIE—International Society for Optical Engineering., vol. 10136, Mar. 10, 2017. 12 pages.

Ronneberger, et al., "U-Net: Convolutional Networks for Biomedical Image Segmentation," Medical Image Computing and Computer-Assisted Intervention—MICCAI 2015—18th International Conference. Nov. 18, 2015, Springer International Publishing, arXiv:1505.04597v1, May 18, 2015. 8 pages.

Yu, et al., "Automated Melanoma Recognition in Dermoscopy Images via Very Deep Residual Networks," IEEE Transactions on Medical Imaging. Dec. 2016. 12 pages.

Akselrod-Ballin, et al., "A Region Based Convolutional Network for Tumor Detection and Classification in Breast Mammography," Springer International Publishing AG, 2016, G. Cameiro et al. (Eds.): Labels 2016/DLMIA 2016, LNCS 10008, pp. 197-205.

Gram, et al., "The Tabar classification of mammographic parenchymal patterns," Elsevier, European Journal of Radiology 24 (1997), pp. 131-136.

Kallenberg, et al., "Unsupervised Deep Learning Applied to Breast Density Segmentation and Mammographic Risk Scoring," IEEE Transactions on Medical Imaging, vol. 35, No. 5, May 2016. pp. 1322-1331.

Winkel, et al., "Mammographic density and structural features can individually and jointly contribute to breast cancer risk assessment in mammography screening: a case-control study," BMC Cancer (2016) DOI 10.1186/s12885-016-2450-7. pp. 1-12.

Communication pursuant to Article 94(3) EPC received for EP Application No. 18719271.1, dated Jun. 21, 2021. 10 pages.

Communication pursuant to Article 94(3) EPC received for EP Application No. 18719272.9, dated Jun. 21, 2021. 8 pages.

\* cited by examiner

MALIGNANCY ASSESSMENT FOR TUMORS

FIELD

The present invention relates to deep learning for automated assessment of malignancy of lesions.

BACKGROUND

Digital mammography is an X-ray system in which the X-ray film is replaced with an electronic system that convert X-rays into images of the human breast. An important procedure prior to image analysis is image segmentation, the slicing of an image into useful and meaningful segments for the ease of analysis. This procedure is often challenging, and the quality of the image may cause difficulty when it comes to accurately and precisely detecting abnormalities 15 or diseases, thus effecting the determination of diagnosis and therapeutic preparation.

Meaningful medical image data plays a key part in the stage of cancer identification and impacts patient treatment. In determining whether one or more lesions are benign or malignant, medical professionals use a system called classification, a method of descriptively assigning objects into a predefined set of categories. This system allows professionals to categorise lesions by possibility of malignancy. Although manual classification has reduced levels of miscommunication and improved monitoring, drawbacks are yet present. Disadvantages of such a traditional determination method include time-consumption, due to the possibility of additional evaluations and manual screening, and possible classification error, due to fault of the human eye, leading to false-positive and false-negative results, which may cause psychological and physiological effects.

SUMMARY OF INVENTION

Aspects and/or embodiments seek to provide a method, apparatus, and system for the automated assessment of malignancy of lesions.

According to a first aspect, there is provided a computer-aided method of malignancy assessment of lesions, the method comprising the steps of: receiving input data; performing a first analysis on the input data to identify one or more lesions, generating a probability map for the one or more lesions from the input data; performing a second analysis on the input data to obtain a malignancy probability mask for the input data; and generating an overlay for the input data by combining the lesion probability map with the malignancy probability mask.

Conventional segmentation methods for identifying and assessing lesions rely on an expert, usually a radiologist, providing a seed region or starting point. Often, the radiologist will segment the entire image without any computerised input, which can lead to errors owing to mistakes, carelessness, human error, and/or details too fine for the human eye to detect. Conversely, the method disclosed herein is operable to segment a region without any prior input other than an image.

Conventional methods rely on some form of initial seed information or feature extraction. These methods are also interactive and require a radiologist to identify areas or perform particular tasks to begin with. In contrast, with this method a radiologist does not need to provide any inputs to initiate or prepare for the analysis which therefore improves time efficiency of the analysis. Additionally, by enabling the use of a malignancy model and a segmentation simultaneously, this method eliminates or at least reduces the chances of false positives.

Optionally, the step of performing the first analysis on the input data is performed through a sliding window. Optionally, the step of performing the second analysis is performed substantially simultaneously to the step of performing the first analysis.

Optionally, the first analysis is performed using one or more Fully Convolutional Networks (FCNs). Optionally, the or each FCN comprises one or more convolutional layers. Optionally, the or each FCN comprises one or more hidden representations. Optionally, the or each FCN comprises one or more activation layers, the one or more activation layers comprising one or more rectified linear units (ReLU) and/or exponential linear units (ELU). Optionally, the or each FCN comprises one or more sigmoid activation layers and/or softmax functions for the or each segmented region.

Optionally, the second analysis is performed using one or more Convolutional Neural Networks (CNNs). Optionally, the one or more CNNs are operable to distinguish between a malignant lesion and/or a benign lesion and/or typical tissue. Optionally, the one or more CN Ns are operable to generate a malignancy model.

Convolutional networks are powerful tools inspired by biological neural processes, which can be trained to yield hierarchies of features and are particularly suited to image recognition.

Convolutional layers apply a convolutional operation to an input, and pass the results to a following layer. With training, FCNs and CNNs can achieve expert-level accuracy or greater with regard to segmenting and assessing anatomical and/or pathological regions and/or lesions in digital medical images such as mammograms.

Optionally, the overall prediction score is a mean score across a plurality of patches.

By applying a mean calculation across a plurality of patches, the number of errors and/or inaccuracies may be reduced. An incorrect calculation for one pixel in an overlapping area may be at least partially mitigated by a correct calculation once the overlapping area is analysed again.

Optionally, the input data comprises medical image data. Optionally, the medical image data comprises one or more mammograms. Optionally, the input data comprises one or more Digital Imaging and Communications in Medicine (DICOM) files.

FCNs can also analyse medical images far more quickly than a human expert, and hence increase the number of medical images analysed overall. Therefore a problem, for example the growth of a cancerous tumour, can be detected more quickly than waiting for a human expert to become available and hence treatment may begin earlier. The identification of regions of interest, which may include lesions, may therefore aid screening and clinical assessment of breast cancer among other medical issues. Earlier diagnosis and treatment can reduce psychological stress to a patient and also increase the chances of survival in the long term.

Optionally, the output data comprises an overlay. Optionally, the overlay comprises a segmentation outline and/or probability map showing one or more locations of one or more segmented regions.

Providing a clear and accurate segmentation of lesion regions can be very helpful when reviewing a medical image, for example a mammogram. This may be especially relevant if there is reason to suspect there is a medical issue with a patient, for example a swollen area which is larger than it was in previous scans. Such changes may be more easily detectable if the different lesion regions are clearly segmented.

Optionally, voids within the segmentation outline are operable to be removed. Optionally, one or more probability masks are generated for the one or more segmented regions. Optionally, one or more of the one or more probability masks are converted to one or more binary masks. Optionally, the conversion of the one or more probability masks to one or more binary masks is performed by thresholding the probabilities. Optionally, one or more parts of the one or more binary masks are removed with reference to an assigned threshold.

If a lesion region is detected and segmented, it is possible that a region within that segmentation is incorrectly identified or not identified at all. Therefore, there may be a void within the pectoral muscle segmentation, or a different segmented region which is too small to have been correctly identified as measured against a predetermined threshold. In order to correct this error that part of the segmentation may be removed. For ease of further downstream analysis, the one or more probability masks may be in the form of one or more probability maps. The one or more binary masks may be in the form of one or more overlays as described herein. The one or more binary masks may further comprise one or more quantized masks. The or any assigned threshold referred to herein may be established through trial and error, expert advice, and/or a tuning process performed before, during, and/or after the training process.

Optionally, the one or more binary masks are upscaled to the original size of the input data. Optionally, the one or more binary masks are stored in the form of a DICOM file. Optionally, the one or more binary masks comprise one or more identifications of masses and/or calcifications. Optionally, the segmented regions comprise at least part of a human breast area.

As a DICOM file is conventionally used to store and share medical images, conforming to such a standard allows for easier distribution and future analysis of the medical images and/or any overlays or other contributory data. The one or more binary masks may be stored as part of a DICOM image file, added to an image file, and/or otherwise stored and/or represented according to the DICOM standard or portion of the standard.

Lesions, which may comprise one or more cancerous growths, masses, abscesses, lacerations, calcifications, and/or other irregularities within biological tissue, can cause serious medical problems if left undetected. Such lesions are often conventionally detected and/or analysed through a medical scan of a patient, which generates one or more medical images such as a mammogram. Therefore, it is advantageous if such lesions are operable to be segmented, and hence reviewed with greater accuracy by a medical professional. By also assessing the probability of malignancy of lesions, appropriate medical action may be taken with the required urgency. Patients with benign lesions, or no lesions at all, may also be spared psychological pain from the uncertainty of knowing the danger that a lesion poses to their future health.

According to a further aspect, there is provided an apparatus operable to perform the method disclosed herein. According to a further aspect, there is provided a system operable to perform the method disclosed herein.

Such an apparatus and/or system may be installed in or near hospitals, or connected to hospitals via a digital network, to reduce waiting times for medical images to be analysed. Patients may therefore be spared stress from not knowing the results of a medical scan, and may receive treatment more quickly if required. The apparatus and/or system and/or method disclosed herein may further form a constituent part of a different arrangement, for example detecting and/or segmenting different objects, environments, surroundings, and/or images.

According to a further aspect, there is provided a computer program product operable to perform the method and/or apparatus and/or system of any preceding claim.

Through the use of a computer or other digital technology, segmentation of lesions from medical images and the assessment thereof may be performed with greater accuracy, speed, and reliability than relying on a human expert. Therefore, a greater number of medical images may be reviewed, reducing backlogs for experts and further reducing errors made when the medical images themselves are actually reviewed.

According to a further aspect, there is provided a method of training a neural network to assess malignancy, the method comprises receiving input data, performing a first analysis on the input data to identify one or more lesions, generating a probability map for the one or more lesions from the input data, performing a second analysis on the input data to obtain a malignancy probability mask for the input data; and using the lesion probability map and malignancy probability map to train the neural network.

BRIEF DESCRIPTION OF DRAWINGS

Embodiments will now be described, by way of example only and with reference to the accompanying drawings having like-reference numerals, in which.

SPECIFIC DESCRIPTION

Figure 1:
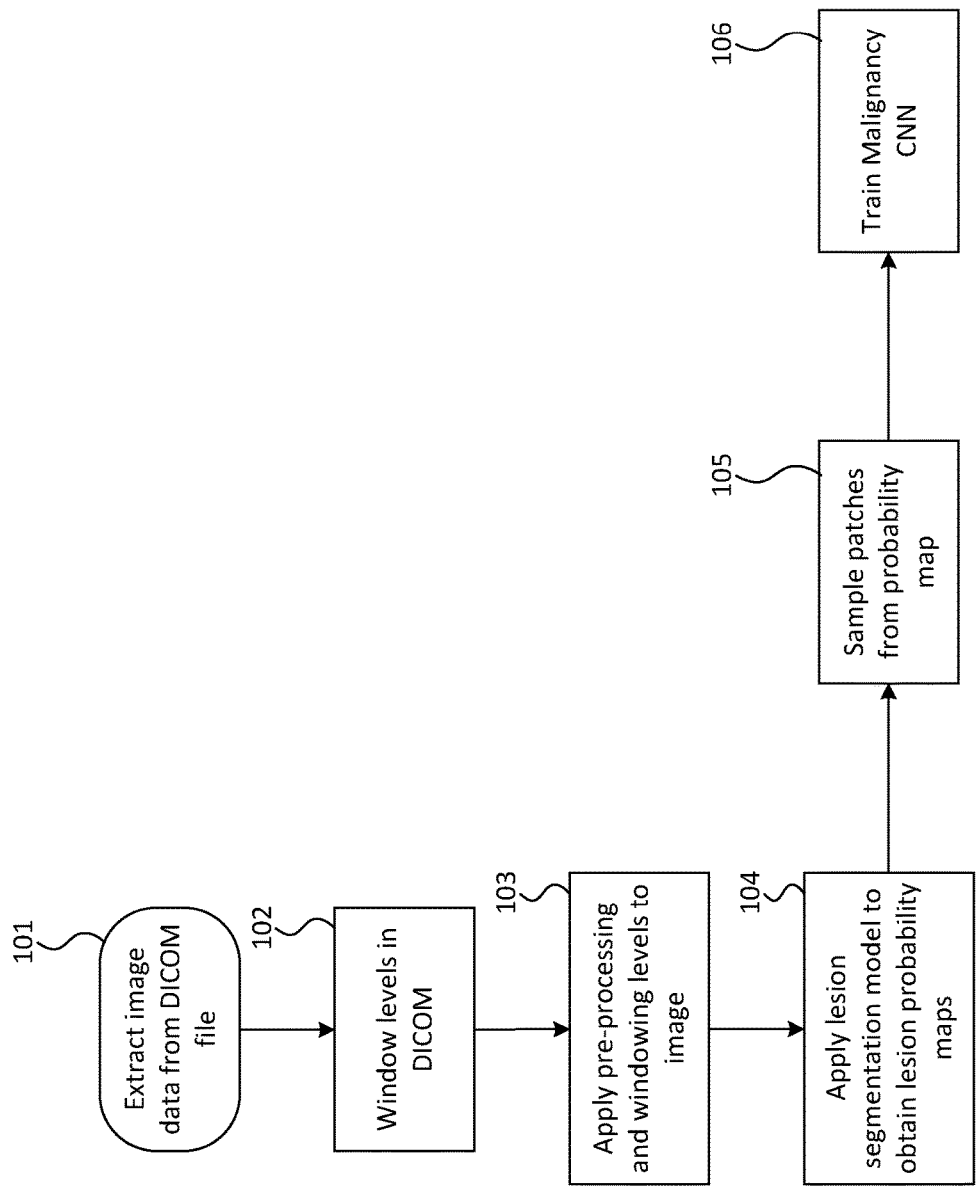
FIG. 1 shows a training procedure for malignancy prediction.

Referring to FIG. 1, a first embodiment will now be described with reference to a training procedure. In this embodiment, a Digital Imaging and Communications in Medicine (DICOM) file is provided as input data 101. DICOM is a conventional standard for transmitting and storing medical images, for example a mammogram. Image data is then extracted from the DICOM file and an image is generated.

The image then undergoes a pre-processing stage 103. The pre-processing stage may comprise windowing the image data to a predetermined windowing level. The windowing level defines the range of bit values considered in the image. Medical images are conventionally 16-bit images, wherein each pixel is represented as a 16-bit integer ranging from 0 to $2^{16}-1$, i.e. $[0, 1, 2, \ldots, 65535]$. The information content is very high in these images, and generally comprises more information than what the human eye is capable of detecting. A set value for the window level is typically included within the DICOM file 102.

It can be important to maintain image resolution. In this embodiment conventional graphics processing unit (GPU) constraints require that the image is divided into a plurality of patches in order to maintain resolution. Each patch is then provided to a Fully Convolutional Network (FCN). The larger the patch, the more context that can be provided but some precision may be lost. For example, in the case of a large image comprising a small tumour, if the FCN is instructed that somewhere in this patch there is a tumour, the network would need to learn how to find it first before it can be classified. In this embodiment patch sizes of 300×300 pixels are used, although larger and smaller patch sizes may be used.

In order to ensure that a prediction for each patch corresponds to a final output probability mask based on mean values for each pixel, a sliding window arrangement is used. In order to use this arrangement, models may be trained on smaller patches sampled from an image. At "prediction/test time", i.e. after the model has been trained, a prediction is required for every pixel of the image, but the input to the model can only be a smaller patch owing to conventional hardware constraints. Therefore, the full image can be divided up into smaller patches and fed individually into the FCN. The model "slides" over the full images in a sliding window fashion and outputs a prediction for each patch. The outputs are then stitched together to generate an output map. Therefore once training is complete, at prediction time the full image is divided into patches in the same sliding window fashion. For example, if each patch is 100×100 pixels every time we slide, we move the patch with a specific number of pixels to the side ("the stride"). The second patch may comprise some overlap with a previous patch. Each patch is classified and that probability is given to every pixel within the patch. For example, if the probability of a patch being cancerous is 0.9, then every pixel in that patch is labelled as 0.9. If there is overlap, the mean of the number of overlapping pixels is calculated, although other arithmetic and/or mathematical operators may be used.

The FCN may comprise any combination of one or more convolutional, hidden representation, activation, and/or pooling layers. The activation layer in this embodiment is in the form of a sigmoid activation layer. The FCN is trained to generate such probability mask by providing a set of input values and associated weights. The probability mask is generated taking the mean for every pixel from the patches to form a final output probability mask 104.

During training of the FCN, a correct class for each value is known, and hence it is possible to compare the FCN's calculated output probability mask to the correct values. An error term or loss function for each node in the FCN can then be established, and the weights adjusted, so that for future input values the output probability mask is closer to the correct value. Backpropagation techniques can be used in the training schedule for the or each neural network.

The model is trained using backpropagation and forward pass through the network. The loss function for dense training is the sum over spatial dimensions of the loss functions of the individual pixels.

$L(x) = \Sigma_{i,j} l'(x_{i,j})$ here L(x) is the loss over the whole image and l'($x_{i,j}$) is the loss for the pixel at i, j. This enables the system to automatically identify one or more tumours from the image created by the system.

The loss function may be the DICE loss, which is defined as $$L_{DSC} = \frac{2\sum_{i}^{N} s_i r_i}{\sum_{i}^{N} s_i + \sum_{i}^{N} r_i}$$

where $s_i$ and $r_i$ represent the continuous values of the prediction map∈[0, . . . , 1] and the ground truth at each pixel i, respectively. Alternatively, a cross-entropy can be used. The cross-entropy loss for the pixel at i, j is defined as $$L_{CE} = -\sum_{c=1}^{C} y * \log(s)$$

where C is the number of classes, y∈{0,1} is the binary indicator for class c, and s is the score for class c. The loss for the full image, x, is defined as the sum over all the losses for the pixels:

$$L_{CE}(x) = \sum_{i,j} \left( -\sum_{c=1}^{C} y * \log(s) \right)$$

Once the probability mask has been generated, which in this embodiment may be in the form of a probability map, one or more patches from the probability map are sampled 105. The sampling may be proportional to the probability of the presence of lesions, in particular the sampling may be taken from areas with a higher probability of being a lesion as defined by a predetermined threshold. Alternatively, Poisson sampling or uniform sampling may be used to sample patches from the probability map. Poisson sampling may give a better coverage of all of the breast tissue. The probability map in this embodiment is in the form of a tensor of the same size as the input image, where each element is a probability of belonging to a class. A patch may comprise an entire probability map, or a portion of the probability map. Using one or more of these sampled patches, a convolutional neural network (CNN) may be trained to generate a malignancy model 106, which in turn generates a malignancy mask. The CNN may also be trained using the results of a different process, for example a Random Forest based candidate selector or any similar lesion detection method.

The malignancy mask can be generated through thresholding. For example, considering a malignancy model with three classes ["A", "B", "C"]. A pixel in the output tensor comprises three values [0.3, 0.3, 0.4]. Therefore, this example would result in a probability vector for that pixel of: 0.3 for class A, 0.3 for class B, and 0.4 for class C.

Figure 2:
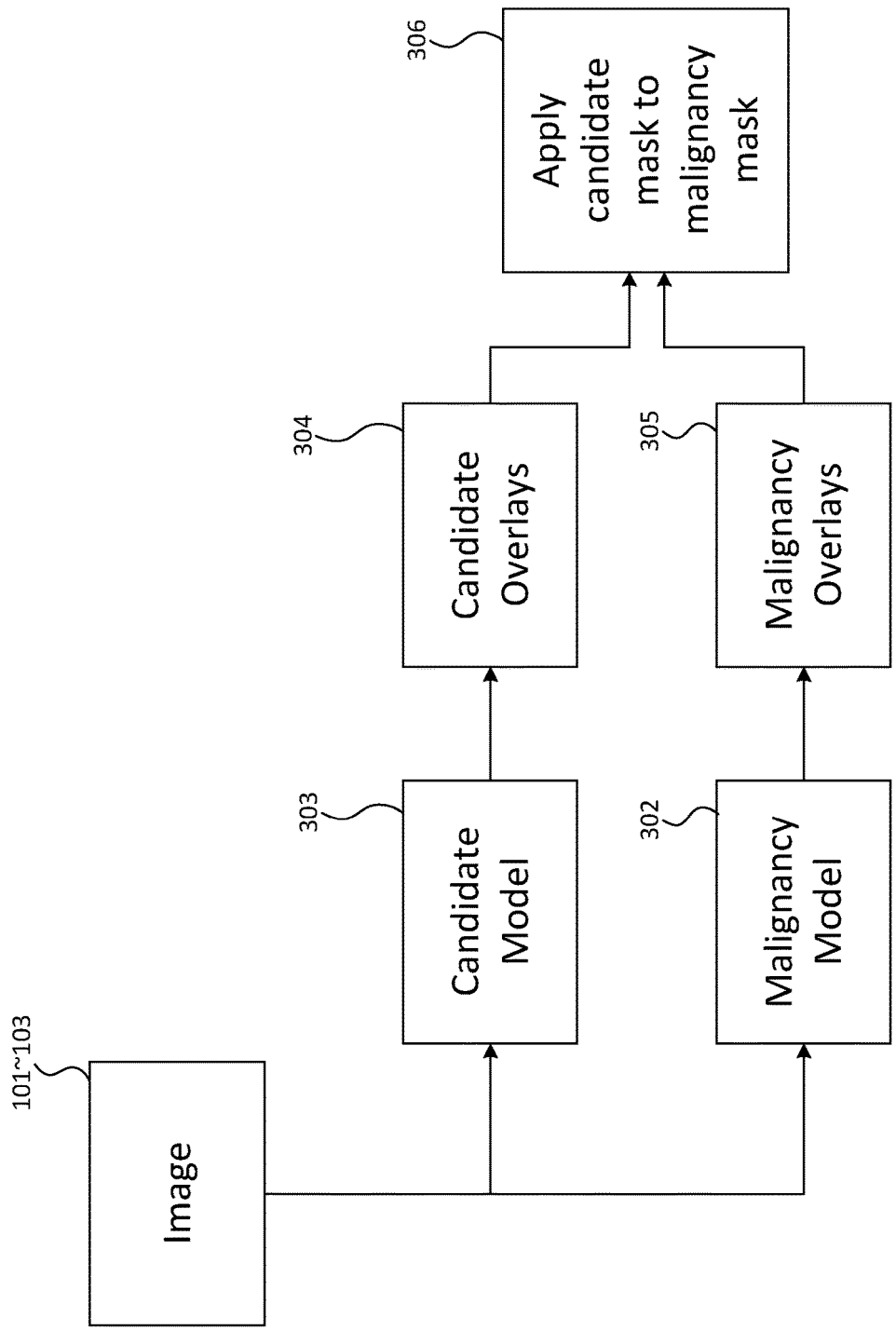
FIG. 2 shows a run time procedure for malignancy prediction.
Figure 3:
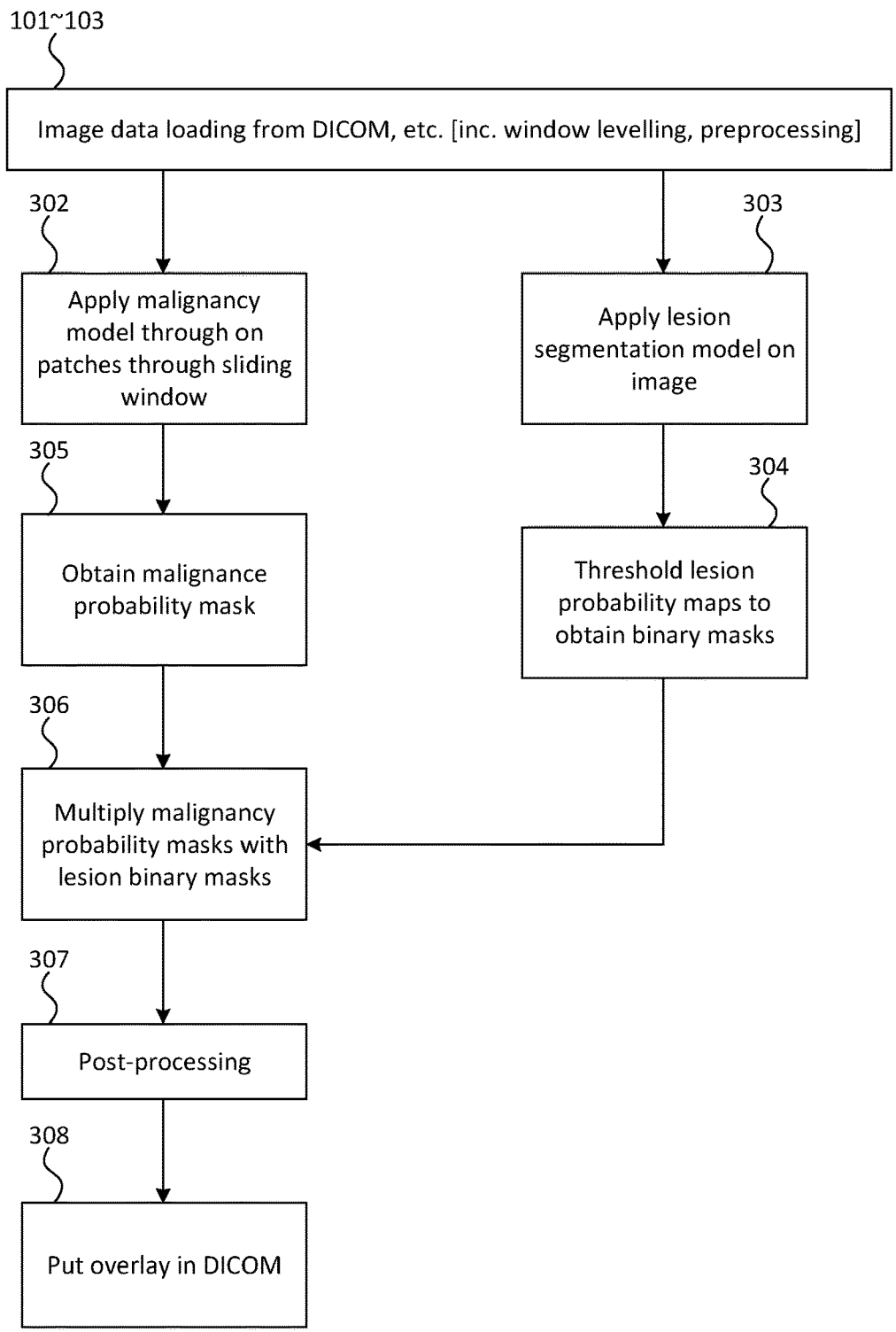
FIG. 3 shows a more detailed example of a run time procedure for malignancy prediction.

FIGS. 2 and 3 show an example of a run time procedure for malignancy prediction. This may also be referred to as prediction time and/or test time. Once a CNN or other appropriate network has been trained as above, the malignancy of lesions may then be predicted with greater accuracy. One or more patches may be provided to the CNN through the use of a sliding window analysis arrangement 302. As depicted in step 303, a lesions segmentation model is applied to the image. The or each probability mask from the FCN is then converted to one or more binary masks during a post-processing stage 304. The conversion from a probability mask to binary mask may be through thresholding the probabilities. Small areas in the binary mask may be removed. If the area (which may be represented by an identified number of pixels) is smaller than a specific predetermined threshold, then the area may be removed from the binary mask entirely. Similarly, holes in the segmentation itself may be removed. If a segmentation has an area of zeros, entirely surrounded by ones, then the zeros may be set to ones according to a predetermined threshold value for the area.

During a prediction, an image is analysed using both the CNN-generated malignancy mask and the FCN-generated probability map. During run time, the malignancy model and the lesion segmentation model process the image simultaneously. The probability map is then used to select one or more relevant parts of the malignancy mask. Such a selection may be provided through multiplying the malignancy mask 305 with the one or more binary masks 306. The result then undergoes a post-processing stage 307, during which an overlay is generated. The overlay may comprise any markings one or more parts of the original image, for example by outlining different areas of human breast tissue, regions of interest, and/or marking one or more levels of malignancy if a lesion is detected and can be stored in the DICOM image 308.

The generation of the overlay is an entirely automated process, and requires no human action other than the input of a data to be analysed. Conventional segmentation methods rely on an expert, usually a radiologist, providing a seed region, starting point or some form of feature engineering. Conversely, the method disclosed herein is operable to segment a region and hence assess malignancy without any prior input other than an image.

Mammography is a medical imaging modality widely used for breast cancer detection. Mammography makes use of "soft" X-rays to produce detailed images of the internal structure of the human breast—these images are called mammograms and this method is considered to be the gold standard in early detection of breast abnormalities which provide a valid diagnosis of a cancer in a curable phase.

Unfortunately, the procedure of analysing mammograms is often challenging. The density and tissue type of the breasts are highly varied and in turn present a high variety of visual features due to patient genetics. These background visual patterns can obscure the often tiny signs of malignancies which may then be easily overlooked by the human eye. Thus, the analyses of mammograms often leads to false-positive or false-negative diagnostic results which may cause missed treatment (in the case of false negatives) as well as unwanted psychological and sub-optimal downstream diagnostic and treatment consequences (in the case of false positives).

Most developed countries maintain a population-wide screening program, comprising a comprehensive system for calling in women of a certain age group (even if free of symptoms) to have regular breast screening. These screening programs require highly standardized protocols to be followed by experienced specialist trained doctors who can reliably analyse a large number of mammograms routinely. Most professional guidelines strongly suggest reading of each mammogram by two equally expert radiologists (also referred to as double-reading). Nowadays, when the number of available radiologists is insufficient and decreasing, the double-reading requirement is often impractical or impossible.

When analysing mammograms, the reliable identification of lesion structures is important for visual evaluation and especially for analytic assessment of visual features based on their anatomic location and their relation to anatomic structures, which may have profound implications on the final diagnostic results. In the case that anatomic structures appear distorted they may also indicate the presence of possible malignancies.

Conventional X-ray is a medical imaging modality widely used for the detection of structural abnormalities related to the air containing structures and bones, as well as those diseases which have an impact on them. Conventional X-ray is the most widely used imaging method and makes use of "hard" X-rays to produce detailed images of the internal structure of the lungs and the skeleton. These images are called roentgenograms or simply X-rays.

Unfortunately, the procedure of analysing X-rays is often challenging, especially when analysing lung X-rays in order to detect infectious disease (e.g. TB) or lung cancer in early stage.

Most developed countries maintain a population-wide screening program, comprising a comprehensive system for calling in the population of a certain age group (even if free of symptoms) to have regular chest X-ray screening. These screening programs require highly standardized protocols to be followed by experienced specialist trained doctors who can reliably analyse a large number of X-rays routinely.

When analysing X-ray images, the reliable identification of lesion structures is important for visual evaluation and especially for analytic assessment of visual features based on their anatomic location and their relation to anatomic structures, which may have profound implications on the final diagnostic results. In the case that anatomic structures appear distorted they may also indicate the presence of possible malignancies.

Cross-sectional medical imaging modalities are widely used for detection of structural or functional abnormalities and diseases which have a visually identifiable structural impact on the human internal organs. Generally the images demonstrate the internal structures in multiple cross-sections of the body. The essence of the most widely used cross-sectional techniques are described below.

Computed tomography (CT) is a widely used imaging method and makes use of "hard" X-rays produced and detected by a specially rotating instrument and the resulted attenuation data (also referred to as raw data) are presented by a computed analytic software producing detailed images of the internal structure of the internal organs. The produced sets of images are called CT-scans which may constitute multiple series with different settings and different contrast agent phases to present the internal anatomical structures in cross sections perpendicular to the axis of the human body (or synthesized sections in other angles).

Magnetic Resonance Imaging (MRI) is an advanced diagnostic technique which makes use of the effect magnetic field impacts on movements of protons which are the utmost tiniest essential elements of every living tissue. In MRI machines the detectors are antennas and the signals are analysed by a computer creating detailed images of the internal structures in any section of the human body. MRI can add useful functional information based on signal intensity generated by the moving protons.

However, the procedure of analysing any kind of cross-sectional images is often challenging, especially in the case of oncologic disease as the initial signs are often hidden and appearance of the affected areas are only minimally differed from the normal.

When analysing cross sectional scans, diagnosis is based on visual evaluation of anatomical structures. The reliable assessment, especially for analytic assessment, of visual appearance based on their anatomic location and their relation to anatomic structures, may have profound implications on final diagnostic results. In the case that anatomic structures appear distorted they may also indicate the presence of possible malignancies.

Generally, in the case of all diagnostic radiology methods (which include mammography, conventional X-ray, CT, MRI), the identification, localisation (registration), segmentation and classification of abnormalities and/or findings are important interlinked steps in the diagnostic workflow.

In the case of ordinary diagnostic workflows carried out by human radiologists, these steps may only be partially or sub-consciously performed but in the case of computer-based or computer-aided diagnoses and analyses the steps often need to be performed in a clear, concrete, descriptive and accurate manner.

Locality and classification may define and significantly influence diagnoses. Both locality and classification may be informed by segmentation in terms of the exact shape and extent of visual features (i.e. size and location of boundaries, distance from and relation to other features and/or anatomy). Segmentation may also provide important information regarding the change in status of disease (e.g. progression or recession).

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training, and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; fully convolutional network or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Developing a machine learning system typically consists of two stages: (1) training and (2) production. During the training the parameters of the machine learning model are iteratively changed to optimise a particular learning objective, known as the objective function or the loss. Once the model is trained, it can be used in production, where the model takes in an input and produces an output using the trained parameters.

Any system feature as described herein may also be provided as a method feature, and vice versa. As used herein, means plus function features may be expressed alternatively in terms of their corresponding structure.

Any feature in one aspect of the invention may be applied to other aspects of the invention, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention claimed is:

1. A computer-aided method of malignancy assessment of lesions, the method comprising:
   receiving input data;
   performing a first analysis on the input data to identify one or more lesions;
   generating a probability map for the one or more lesions from the input data;
   performing a second analysis on the input data to obtain a malignancy probability mask for the input data, wherein the malignancy probability mask comprises the form of a tensor having probabilities for different lesion classes assigned to each of one or more pixels from the input data; and
   generating an overlay for the input data by combining the lesion probability map with the malignancy probability mask.

2. The method of claim 1, wherein performing the first analysis on the input data is performed through a sliding window.

3. The method of claim 1, wherein performing the second analysis is performed substantially simultaneously to performing the first analysis.

4. The method of claim 1, wherein the first analysis is performed using one or more Fully Convolutional Networks (FCNs), and/or the second analysis is performed using one or more Convolutional Neural Networks (CNNs).

5. The method of claim 4, wherein the or each FCN comprises one or more convolutional layers and/or one or more hidden representations.

6. The method of claim 4, wherein the or each FCN comprises one or more activation layers, the one or more activation layers comprising one or more rectified linear units (ReLU) and/or exponential linear units (ELU).

7. The method of claim 4, wherein the or each FCN comprises one or more sigmoid activation layers and/or softmax functions for each of one or more segmented regions.

8. The method of claim 4, wherein the one or more CNNs are operable to distinguish between a malignant lesion and/or a benign lesion and/or typical tissue.

9. The method of claim 4, wherein the one or more CNNs are operable to generate a malignancy model.

10. The method of claim 1, wherein the input data further comprises one or more patches, the method further comprising:
    calculating an overall prediction score for the one or more patches or each of the one or more patches; and
    determining an overall prediction score which is a mean score across a plurality of the one or more patches.

11. The method of claim 1, wherein the input data comprises medical image data and/or one or more Digital Imaging and Communications in Medicine (DICOM) files.

12. The method as claimed in claim 11, wherein the medical image data comprises one or more mammograms.

13. The method of claim 1, wherein the overlay comprises a selection of one or more elements of the malignancy probability mask based on an application of the probability map.

14. The method of claim 13, wherein the overlay comprises a segmentation outline and/or probability map showing one or more locations of one or more segmented regions.

15. The method of claim 14, further comprising removing voids within the segmentation outline.

16. The method of claim 14, further comprising one or more of:
    generating one or more probability masks for the one or more segmented regions;
    converting one or more of the one or more probability masks to one or more binary masks, wherein the one or more binary masks comprise one or more identifications of masses and/or calcifications, wherein the converting is performed by thresholding the probabilities; and
    removing one or more parts of the one or more binary masks with reference to an assigned threshold.

17. The method of claim 16, wherein the one or more binary masks are one or both upscaled to the original size of the input data and/or stored in the form of a DICOM file.

18. An apparatus operable to perform the method of claim 1.

19. A computer program product including one or more non-transitory machine readable mediums encoded with instructions that when executed by one or more processors cause a process to be carried out for assessing malignancy of lesions, the process comprising receiving input data;
    performing a first analysis on the input data to identify one or more lesions;
    generating a probability map for the one or more lesions from the input data;
    performing a second analysis on the input data to obtain a malignancy probability mask for the input data, wherein the malignancy probability mask comprises the form of a tensor having probabilities for different lesion classes assigned to each of one or more pixels from the input data; and
    generating an overlay for the input data by combining the lesion probability map with the malignancy probability mask.

20. A method of training a neural network to assess malignancy, the method comprising:
    receiving input data;
    performing a first analysis on the input data to identify one or more lesions;
    generating a probability map for the one or more lesions from the input data;
    performing a second analysis on the input data to obtain a malignancy probability mask for the input data, wherein the malignancy probability mask comprises the form of a tensor having probabilities for different lesion classes assigned to each of one or more pixels from the input data; and
    using the lesion probability map and malignancy probability mask to train the neural network.

* * * * *